United States Patent [19]

Bonsen et al.

[11] 4,265,874
[45] May 5, 1981

[54] METHOD OF DELIVERING DRUG WITH AID OF EFFERVESCENT ACTIVITY GENERATED IN ENVIRONMENT OF USE

[75] Inventors: Pieter Bonsen, Los Altos, Calif.; Patrick S. Wong, Kowloon, Hong Kong; Felix Theeuwes, Los Altos, Calif.

[73] Assignee: Alza Corporation, Palo Alto, Calif.

[21] Appl. No.: 143,644

[22] Filed: Apr. 25, 1980

[51] Int. Cl.³ .............................. A61K 9/46; A61J 1/00
[52] U.S. Cl. ....................................... 424/15; 128/260; 424/14; 424/16; 424/22; 424/44; 424/274
[58] Field of Search .................... 424/14, 19, 22, 44, 424/274; 128/260

[56] References Cited

U.S. PATENT DOCUMENTS

| 536,155 | 3/1895 | Noyes | 424/44 |
|---|---|---|---|
| 2,211,485 | 8/1940 | Zimmermann | 424/44 |
| 2,312,381 | 3/1943 | Bickenheuser | 424/44 |
| 3,062,715 | 11/1962 | Reese | 424/44 |
| 3,131,123 | 4/1964 | Masquelier | 424/44 |
| 3,136,692 | 6/1964 | Bandelin | 424/44 |
| 3,495,001 | 2/1970 | Leonards | 424/44 |
| 3,676,549 | 7/1972 | Higuchi et al. | 424/44 |
| 3,764,668 | 10/1973 | Higuchi et al. | 424/44 |
| 3,773,922 | 11/1973 | Gergely | 424/44 |
| 3,845,770 | 11/1974 | Theeuwes et al. | 128/260 |
| 3,887,700 | 6/1975 | Boncey et al. | 424/44 |
| 3,916,899 | 11/1975 | Theeuwes et al. | 128/260 |
| 4,008,719 | 2/1977 | Theeuwes et al. | 128/260 |
| 4,036,228 | 7/1977 | Theeuwes | 128/260 |
| 4,088,864 | 5/1978 | Theeuwes et al. | 219/121 |
| 4,111,201 | 9/1978 | Theeuwes | 128/260 |
| 4,160,452 | 7/1979 | Theeuwes | 128/260 |

FOREIGN PATENT DOCUMENTS

| 1981834 | 10/1934 | Australia | 424/44 |
|---|---|---|---|
| 5391M | 10/1967 | France | 424/44 |
| 917456 | 2/1963 | United Kingdom | 424/44 |
| 1123316 | 8/1968 | United Kingdom | 424/44 |

OTHER PUBLICATIONS

Garnham, J. C. et al., Chem. Abstr. 87 #15664q (1977) of PostGrad. Med. J. 1977 53 (617) 126–129 The Different Effects of Sodium Bicarbonate and Aluminum Hydroxide on the Absorption of Indomethacin.
Korkhoffs et al. C.A. 68 #11391h (1968).
Arnold et al., C.A. 74 #123574a (1971).
Allen et al., C.A. 76 #49955y (1972).
Demski et al., C.A. 79 #9889k (1973).
Krasowska C.A. 83 #168378s (1975).
Bartkowics C. A. 83 #379t 83 #15686r )1975).

*Primary Examiner*—Shep K. Rose
*Attorney, Agent, or Firm*—Paul L. Sabatine; Edward L. Mandell; Thomas E. Ciotti

[57] ABSTRACT

A method is disclosed for delivering a drug substantially free of rapid precipitation from an osmotic device. The osmotic device comprises a semipermeable wall surrounding a compartment, housing (1) a drug that exhibits limited solubility under neutral and acid conditions; and (2) a compound capable of evolving carbon dioxide in the presence of an acid in the environment of use. The method comprises, (a) imbibing fluid through the wall into the compartment at a rate determined by the permeability of the wall and the osmotic pressure gradient across the wall, (b) forming in the compartment a basic solution containing drug and compound, which solution is delivered from the compartment through the passageway, (c) reacting the compound with the acid in the environment at the device-environment interface for evolving carbon dioxide, thereby, (d) providing an effervescent suspension in the environment that delivers the drug in a finely dispersed form to the environment of use over time. Also, a composition is disclosed comprising the drug and the compound.

29 Claims, 2 Drawing Figures

METHOD OF DELIVERING DRUG WITH AID OF EFFERVESCENT ACTIVITY GENERATED IN ENVIRONMENT OF USE

FIELD OF THE INVENTION

This invention pertains to a method for delivering a drug that needs assistance in its delivery from an osmotic device. More particularly, the invention relates to an improved method for delivering from an osmotic device a drug, which drug exhibits limited solubilities and precipitates in neutral and acid surroundings, to an exterior acid environment. The improved method comprises creating a basic condition in the device, raising the pH of the exterior environment in the vicinity of the passageway, and producing an effervescent suspension that transports the drug in finely dispersed form away from the device in the environment of use. The invention also concerns compositions comprising the drug and a compound containing a carbon dioxide generating moiety.

BACKGROUND OF THE INVENTION

Osmotic systems manufactured in the form of osmotic devices for delivering a drug to an environment of use are known to the art in U.S. Pat. Nos. 3,845,770 and 3,916,899, both issued to inventors Felix Theeuwes and Takeru Higuchi. A typical system, disclosed in these patents, comprises a semipermeable wall that surrounds a compartment containing a drug. The wall is permeable to an external fluid and substantially impermeable to the passage of drug. There is a passageway through the wall for delivering drug from the system. The system releases drug by fluid being continuously imbibed through the wall into the compartment at a rate determined by the permeability of the wall and the osmotic pressure gradient across the wall to produce a solution containing soluble drug that is dispensed from the system over time.

While the above system is an outstanding invention and represents a pioneer advancement in the delivery art, and while it is endowed with ideal delivery kinetics useful for delivering numerous beneficial drugs at controlled rates and continuously to the environment of use, there is an occasional instance where the delivery kinetics of the system can be unexpectedly improved leading to more desirable results. For example, many antiinflammatory drugs are practically insoluble in acid environments, such as in the gastric fluid of the stomach, and these drugs on their delivery from the system immediately precipitate on contact with the gastric fluid. This phenonemon occurs with precipitating drug accumulating at the exit of the passageway and on the exterior surface of the wall of the system. The precipitated drug impedes the flow of a saturated drug solution through the passageway, and the precipitated drug on the wall also impedes the imbibition of fluid into the system. These phenomena seriously diminish the release of these drugs at meaningful and beneficial rates from the system.

In U.S. Pat. No. 4,036,228, issued to Felix Theeuwes, the patentee discloses an osmotic system embodying a means for delivering drugs that are hard to deliver, particularly drugs that are practically insoluble in aqueous-type fluids. The means consists essentially in charging the system with an effervescent couple comprising an acidic component and a basic component. In operation when the system is in a fluid environment, the couple imbibes fluid into the system, thereby wetting the couple, causing it to react and produce in the system an effervescent solution. The effervescent solution creates a neutral condition in the system and it dispenses the drug from the system. The patent does not address itself to the delivery of drugs that exhibit limited solubilities in acidic environments, the use of only the basic components, and the production of effervescence in the environment of use.

Thus, in the light of the above discussion, it will be readily appreciated by those versed in the subject art that a critical need exists for a means for delivering drugs that have limited solubilities in acidic environments, especially where the means overcomes the tribulations associated with the prior art. Likewise, it will be further appreciated by those skilled in the art, that if a novel and useful method is made available for delivering these drugs, such a method would have a positive value and also represent a substantial contribution to the art.

OBJECTS OF THE INVENTION

Accordingly, in the light of the above presentation, it becomes an immediate object of the invention to provide a novel and useful method for delivering at meaningful rates from an osmotic system, drugs that are difficult to deliver.

Another object of the invention is to provide a method for delivering drug from an osmotic system using a method that overcomes the difficulties associated with the prior art.

Still another object of the invention is to provide a method for dispensing a drug from an osmotic device, which drug has a limited solubility in a fluid that enters the device, yet it is dispensed by the method from the device in a predetermined amount, at a controlled and continuous rate to an environment of use.

Yet still another object of the invention is to provide a method for delivering a drug that is difficult to deliver from an osmotic device, which method comprises using a basic compound that generates carbon dioxide in an exterior acid environment for delivering the drug away from the osmotic delivery device.

Still a further object of the invention is to provide a method for dispensing a drug from an osmotic device, which method can administer a complete pharmaceutical regimen to a human for a particular time period, the use of which requires intervention only for initiation and optional termination of the regimen.

Yet still another object of the invention is to provide a method for delivering a drug that has limited solubility in an acid environment of use to the environment, which method consists essentially of delivering the drug in a finely dispersed form in an effervescent suspension to the environment over a prolonged period of time.

Other objects, features and advantages of the invention will be more apparent to those skilled in the art form a reading of the detailed description of the specification, taken in conjunction with the claims.

SUMMARY OF THE INVENTION

This invention concerns a method for delivering a drug from an osmotic device. The method comprises housing in the compartment of the device a drug that is poorly soluble in aqueous and acid surroundings, and a basic compound having a carbon dioxide generating moiety. The method releases drug by fluid being imbibed into the compartment creating a solution containing drug and compound under hydrostatic pressure, which solution is dispensed through the passageway into an acidic fluid environment of use. In the environment, the compound in the solution on immediate contact with the acid in the environment reacts therewith and generates carbon dioxide gas. This physical activity, and the gas, dispense the drug in a finely dispersed fluffy form from the device, thereby dispensing the drug in the environment of use.

DETAILED DESCRIPTION OF THE INVENTION

Figure 1:
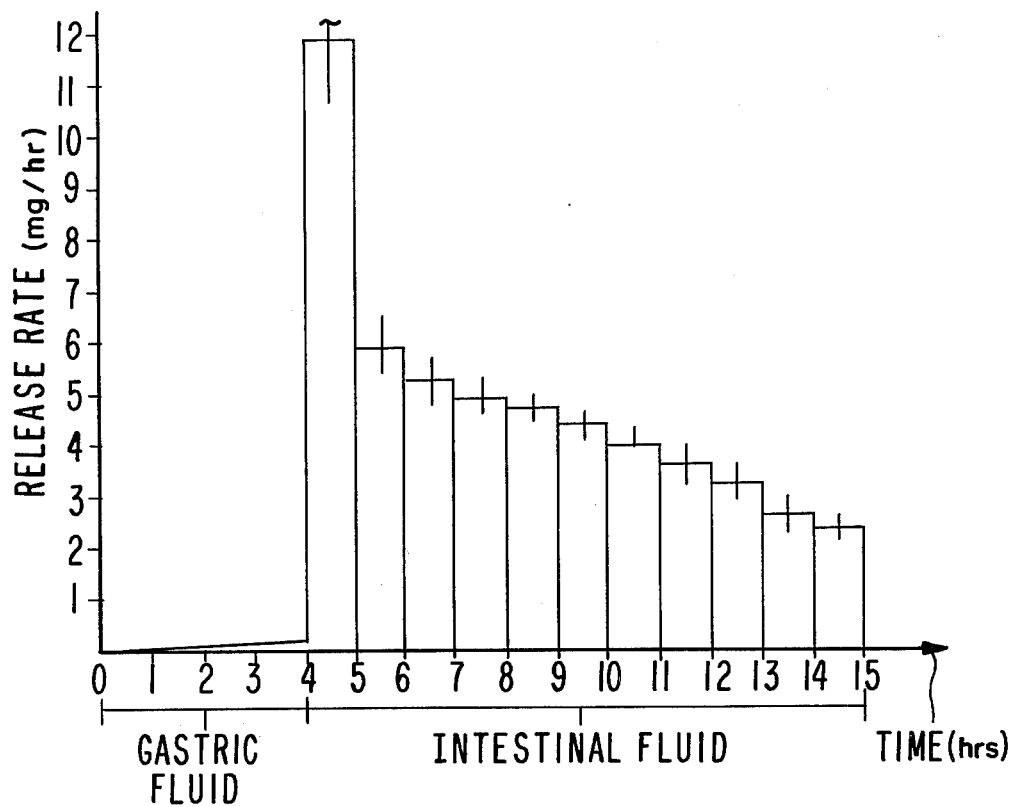

In attaining the objects, features and advantages of this invention, it has now been found, that difficult to deliver drugs can be delivered according to the mode and the manner of the invention. The method of the invention uses an osmotic device for delivering the drug. The osmotic device comprises a wall that surrounds and defines a compartment. The compartment houses a drug, a basic compound having a carbon dioxide generating moiety, and optionally other ingredients. There is a passageway through the wall for dispensing the drug, the compound and the other ingredients from the device.

The wall of the osmotic system is formed of a material that does not adversely affect the drug, the compound, a host, or the environment of use. The wall is formed of a polymeric material that is permeable to the passage of an exterior fluid, such as water and biological fluids, and it is essentially impermeable to the passage of drugs, solutes and the like. The selectively permeable polymers useful for manufacturing the devices are represented by a member selected from the group consisting of cellulose acylate, cellulose diacylate, cellulose triacylate, cellulose acetate, cellulose diacetate, cellulose triacetate, polyamides, polyurethanes, and the like. Suitable semipermeable polymers for manufacturing osmotic devices are disclosed in U.S. Pat. Nos. 3,845,770; 3,916,899; 4,008,719; 4,036,228; and 4,111,210. These patents are assigned to the ALZA Corporation of Palo Alto, California, the assignee of this patent application. In an embodiment, the wall can be a laminate comprising a semipermeable lamina in laminar arrangement with a microporous lamina. The semipermeable lamina is formed of the above described polymers. The microporous lamina has a plurality of micropores and interconnected micropaths for admitting fluid into the device. The microporous lamina can comprise the above polymers housing a pore former that is dissolved, or leached from the lamina, when the device is in operation in the environment of use. The pore formers are non-toxic and they do not react with the materials forming the wall. On their removal from the lamina, the paths formed therein fill with fluid, and these paths become a means for fluid to enter the device. Typical pore formers are represented by sodium chloride, potassium chloride, sorbitol, mannitol, polyethylene glycol, hydroxypropyl methylcellulose, hydroxypropyl butylcellulose, and the like. Osmotic devices having a laminated wall comprising a semipermeable lamina and a microporous lamina are disclosed in U.S. Pat. No. 1,160,452, assigned to the ALZA Corporation.

The expression passageway as used herein, includes an aperture, orifice, bore, hole and the like through the wall. The expression also includes an erodible element in the wall, such as a gelatin plug that erodes and forms a passageway in the environment of use. A detailed description of osmotic passageways, and the maximum and minimum dimensions for passageways are disclosed in U.S. Pat. Nos. 3,845,770 and 3,916,899. These patents are assigned to the ALZA Corporation.

The expression drug as used herein broadly includes any compound, composition of matter, or mixture thereof, that can be delivered from the device to produce a beneficial and useful result. The term drug more specifically includes any substance that produces a local or a systemic effect in animals, avians, pisces, and reptiles. The term animals includes primates, humans, household, sport and farm animals, such as goats, cattle, horses, dogs, cats, and the like. The term animal also includes laboratory animals such as mice, rats, and guinea pigs. The drugs that can be delivered by the method of the invention include inorganic and organic drugs, such as central nervous system acting drugs, hypnotics, sedatives, psychic energizers, tranquilizers, antidepressants, anticonvulsants, muscle relaxants, antiparkinson agents, anesthetics, antiinflammatory agents, local anesthetics, antimalarials, hormones, sympathomimetics, diuretics, antiparasitics, neoplastics, hypoglycemics, ophthalmics, nutritionals, and the like.

The term, in a more preferred embodiment, embraces drugs that are practically insoluble, or have a limited solubility in neutral and acidic environments. That is, these drugs precipitate in such environments. The expression neutral includes water and like biological environments, and the expression acid includes the stomach and the hydrochloric acid produced therein, the vagina and the lactic acid produced therein, and the like. The phrase acidic body fluid as used herein denotes gastric fluid, vaginal fluid and like acid environments in an animal body.

A specific groups of drugs suitable for delivery to the above environments by the method of the invention are the acidic antiinflammatory drugs. The antiinflammatory drugs are represented by arylcarboxylic acid drugs, and enolic acid drugs. Examples of arylcarboxylic acid drugs include alclofenac or 4-allyloxy-3-chlorophenylacetic acid; aspirin or acetylsalicylic acid; fenoprofen or dl-2-(3-phenoxyphenyl)propionic acid; flufenamic acid or 2-(3-trifluoromethylanilino)benzoic acid; ibuprofen or 2(4-isobutylphenyl)propionic acid; indomethacin or 5-methoxy-2-methyl-1-(4'-chlorobenzoyl)-3-indole-acetic acid; ketoprofen or 2-(3-benzoylphenyl) propionic acid; metiazinic acid or 10-methyl-2-phenothiazinylacetic acid; naproxen or d-2-(6'-methoxy-2'-naphthyl)propionic acid; niflumic acid or 3-trifluoromethyl-2-phenyl-aminonicotinic acid; tolmetin or 1-methyl-5-p-toluylpyrrole-2acetic acid; and sulindac or cis-5-fluoro-2-methyl-1-[p-(methylsulfinyl)-benzylidene]indene-3-acetic acid. Examples of enolic acid drugs include azapropazone or 3-dimethylamino-7-methyl-1,2-(n-propylmalonyl)-1-2,dihydro-1,2,4-benzotriazine; phenylbutazone or 3,5-dioxo-4-n-butyl-1,2-diphenylpyrrazolidine; prenazone or 4-prenyl-1,2-diphenyl-3,5-pyrrazolidinedione; sudoxicam or 4-hydroxy-2-methyl-N-(2-thiazolyl)-2H-1,2-benzothiazine-3-carboxamide-1,1-dioxide; and the like. Other antiinflammatory drugs include diclofenac or 2-[2,6-dichlorophenyl)amino] benzeneacetic acid; and peroxicam or 2H-1,2-benzothiazine-3-carboxamide.

Examples of other drugs that are practically insoluble or very slightly soluble in water that can be delivered by the method of the invention include diphenidol, meclizine hydrochloride, prochlorperazine maleate, anisindone, diphenadione, erythrityl tetranitrate, dizoxin, resperpine, acetazolamide, methazolamide, bendroflumethiazide, chlorpropamide, tolazamide, allopurinol, aluminum aspirin, salicylic acid, sodium salicylate, salicylamide, acetaminophen, acetophenetidin, colchicine, mefenamic acid, oxphenbutazone, zomepirac, methotrexate, acetyl sulfisoxazole, hydrocortisone, desoxycorticosterone acetate, cortisone acetate, triaminolone, 17$\beta$-estradiol, 17$\alpha$-hydroxyprogesterone, 19-norprogesterone, prednisolone, progesterone, norethindrone acetate, norethynodrel, zidometacin, and the like.

The amount of drug present in a device will vary depending on the activity and the amount of drug to be administered to the host. Generally, the device will house from 0.5 mg to 3 g or more, with individual devices containing for example 25 mg, 50, 125 mg, 250 mg, 1.5 g and the like. The drug can be in the device in various forms such as dispersion, granule, powder, pressed mass, film, and the like. Also, the drug can be mixed with a binder, diluent, dispersant, stabilizer, dye and the like. The beneficial drugs, their solubilities, their present doses are known to the art in *Pharaceutical Sciences*, by Remington, 15th ed., 1975, published by the Mack Publishing Co., Easton, Penna; *The Drug, the Nurse, the Patient, Including Current Drug Handbook*, 1974-1976, by Falconer, et al, published by Saunder Company, Philadelphia, Penna; in *Physician Desk Reference*, 33rd Ed., 1979, published by Medical Economics Co., Oradell, N.J.; in *Ann. of Allergy*, Vol. 41, pages 75 to 77, 1979; in *Arzneim. Forsch.*, Vol. 25, pages 1629 to 1635, 1975; and in *J. Inter. Med. Res.*, Vol. 7, page 335 to 338, 1979.

The gas generating compound suitable for the purpose of the invention is preferably a solid, basic compound that is pharmaceutically acceptable, and (a) exhibits a concentration gradient across the semipermeable wall and imbibes fluid into the device, (b) acts as a buffer and dissolves in fluid that enters the device forming a solution containing drug, (c) raises outside of the device, the pH of the immediate surrounding area of the passageway high enough to lessen the rate of precipitation of the drug, and (d) reacts, outside the device at the passageway environment interface, with the acid of the environment to produce carbon dioxide effervescence that directs drug away from the device in a finely, dispersed form. The basic compounds include non-toxic metal carbonate and bicarbonate salts, such as alkali metal carbonates and bicarbonates, the alkaline earth carbonates and bicarbonates, and mixtures thereof. The preferred compounds are those soluble in water and produce rapid effervescence on contact with the acid of the environment. A mixture of compounds with different degrees of solubility in water can be use with at least one compound being very soluble in water. Exemplary compounds include lithium carbonate, sodium carbonate, potassium carbonate, lithium bicarbonate, sodium bicarbonate, potassium bicarbonate, magnesium carbonate, calcium carbonate, magnesium bicarbonate and the like. Also useful gas generating compounds are ammonium carbonate, ammonium bicarbonate, ammonium sesquecarbonate, sodium sesquecarbonate and the like. These compounds, when dissolved in water, show a pH greater than 7, usually between 8 and 12. Optionally, it is often desirable to select the drug and the compound free of a common ion effect, so their respective solubilities in a fluid that enters the device are at their maximum. The amount of basic compound, or mixture thereof housed in the compartment generally is about 0.5 mg to 3 g, or more, and more preferably 25 mg to 750 mg. The compounds and their solubilities in water are disclosed in *The Handbook of Chemistry and Physics*, 48th Ed., 1968, published by the Chemical Rubber Co., Cleveland, Ohio.

The drug and the basic compound also can be used mixed with a binder and a lubricant. The drug and the compound are mixed in a water soluble binder, or in a water insoluble binder that releases the drug and compound on contact with water. Typical water soluble binders include poly(ethylene glycol), gelatin, agar, carboxycellulose, ethylmethyl-cellulose, poly(vinyl alcohol), poly(vinylpyrrolidone), water soluble starch derivatives, and the like. Typical lubricants include stearic acid, magnesium stearate, zinc stearate and the like. The amount of binder or lubricant used generally is about 0.1 mg to 150 mg, or more.

The osmotic devices of the invention are manufactured by standard techniques. For example, in one embodiment, the drug is mixed with the basic compound and other ingredients by ballmilling, calendering, stirring and pressing into a preselected shape. The material forming the wall of the device can be applied by dipping, molding or spraying the pressed mixture. One procedure for applying the wall is the air suspension technique. The air suspension technique can be used for manufacturing a wall formed of a single layer, or formed of a multiplicity of layers. The air suspension procedure is described in U.S. Pat. No. 2,799,241; in *J. Am. Pharm. Assoc.*, Vol. 48, pages 451 to 459, 1959; and in ibid, Vol. 49, pages 82 to 84, 1960. An osmotic passageway or aperture through the wall is made by mechanical drilling, laser drilling, punching or cutting with die. A procedure for forming the passageway using a laser is described in U.S. Pat. Nos. 3,916,899 and 4,088,864, both assigned to the ALZA Corporation. Other standard manufacturing procedures are described in *Modern Plastic Encyclopedia*, Vol. 46, pages 62 to 70, 1969; in *Remington's Pharmaceutical Sciences*, 14th Ed., pages 1649 to 1698, 1970, published by Mack Publishing Co., Easton, Penna., and in *The Therapy and Practice of Industrial Pharmacy*, by Lachman, et al, pages 197 to 225, 1970, published by Lea & Febiger Co., Philadelphia, Penna.

DESCRIPTION OF EXAMPLES OF THE INVENTION

The following examples are merely illustrative of the present invention and they should not be considered limiting the scope of the invention in any way, as these examples and other equivalents thereof will become more apparent to those versed in the art in the light of the present disclosure, and the accompanying claims.

EXAMPLE 1

An oral osmotic device for the delivery of a nonsteroidal antiinflammatory drug sodium indomethacin, was manufactured as follows: a drug composition was prepared for housing in the compartment of the device by thoroughly blending 105.2 mg of sodium indomethacin trihydrate, 142 mg of potassium bicarbonate, 5.0 mg of polyvinyl pyrrolidone, and 7.1 mg of stearic acid, and then compressing the homogeneous blend into a precompartment forming drug formulation. Next, the compressed drug formulation was placed in an air suspension machine and coated with a microporous lamina forming composition. The microporous lamina composition comprised 45% by weight of cellulose acetate having an acetyl content of 39.8%, 27.5% by weight of hydroxypropyl methylcellulose, and 27.5% by weight of polyethylene glycol 4000. The lamina was formed from a methylene chloride—95% ethanol solvent (80:20 wt:wt). The microporous lamina was 5 mil thick.

Next, an exterior semipermeable lamina was laminated onto the microporous lamina, in the air suspension machine. The semipermeable lamina forming composition comprised 50% by weight of cellulose acetate having an acetyl content of 39.8% and 50% by weight of cellulose acetate having an acetyl content of 32%. The semipermeable lamina was applied from a solvent mixture comprising methylene chloride and 95% ethanol, 80:20 wt:wt. The systems were dried, and a 10 mil passageway was laser drilled through the laminated wall. The system releases indomethacin at the rate of 8 mg per hour. The device in operation, releases a solution that effervesces on contact with the acidic gastric fluid at the exit end of the passageway, producing carbon dioxide bubbles that disperse the drug in a fluffy state.

EXAMPLE 2

An oral osmotic device for the controlled and continuous delivery of indomethacin was made by following the general procedure described above. In the present device, the compartment housed a drug formulation comprising 56.4% potassium carbonate, 37.6% sodium indomethacin trihydrate, 3% Providone ® and 3% stearic acid. The formulation after compressing had a diameter of 7.93 mm, an area of 1.6 cm$^2$ and a density of 1.65 g/ml. The device had a laminated wall comprising an interior microporus lamina consisting essentially of 45% by weight of cellulose acetate having an acetyl content of 39.8%, 45% by weight of sorbitol, and 10% by weight of polyethylene glycol 400. The lamina was applied from a solvent comprising methylene chloride-methanol-water, 62:35:3 by wt. A semipermeable lamina was laminated onto the microporous lamina, which semipermeable lamina consists of 50% by weight of cellulose acetate having an acetyl content of 39.8%, and 50% by weight of cellulose acetate having an acetyl content of 32%. The lamina was applied from a solvent consisting of methylene chloride and methanol, 80:20 by wt. The microporous forming lamina was 5 mil thick, and the semipermeable lamina 2.4 mil thick. The device had a 9 mil passageway and delivered indomethacin at the rate of 8 mg/hr. The device delivers the drug substantially free of rapid precipitation at the passageway environment interface, and on the wall of the device in the vicinity of the passageway.

EXAMPLE 3

The procedure of Example 2 was repeated with the conditions as described except that the microporous forming lamina was 1 mil thick, the semipermeable lamina 2.7 mil thick, and the rate of release was 8 mg/hr.

EXAMPLE 4

The osmotic device of Example 1 and 2 was manufactured in this example, wherein (a) the microporous lamina was 5 mil thick, the semipermeable lamina was 3.4 mil thick, and the device had a release rate of 6 mg/hr, and (b) a device wherein the microporous lamina was 5 mil thick, the semipermeable lamina was 1.7 mil thick, and the system had a release rate of 12 mg/hr.

EXAMPLE 5

A series of oral osmotic devices for releasing an arylcarboxylic acid antiinflammatory drug in the gastrointestinal tract are prepared according to the invention, wherein the device houses from 40 to 250 mg of sodium indomethacin and more preferably from 85 to 125 mg of sodium indomethacin trihydrate the equivalent of 70 to 100 mg of indomethacin, from 50 to 300 mg of potassium bicarbonate and more preferably from 130 to 190 mg of potassium bicarbonate, 2 to 20 mg of binder, and more preferably 5 to 10 mg. The device has an inner microporous forming lamina weighing 18 to 25 mg with a thickness of 0.10 to 0.16 mm, and an exterior semipermeable lamina weighing 6 to 20 mg with a thickness of 0.035 to 0.100 mm. The device has a passageway of 0.18 mm to 0.38 mm, and releases drug at the rate of 2 to 15 mg/hr.

Figure 2:
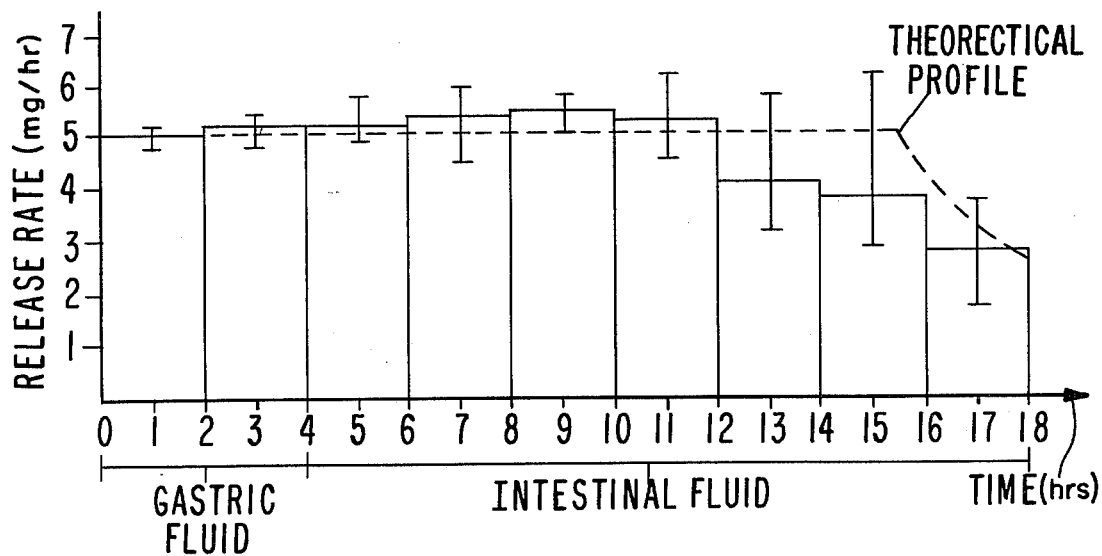

The unexpected benefits produced by the invention are seen in FIG. 1 and FIG. 2. FIG. 1 shows the release of indomethacin from an osmotic device manufactured without a basic gas generating compound. The device releases the drug in the presence of an artifical gastric fluid containing hydrochloric acid, however, the drug precipitates onto the wall of the device and the exit port of the passageway, and it is therefore not observed in the fluid of the environment, which is analyzed on an hourly basis, as displayed in FIG. 1. FIG. 2 shows the release of indomethacin from an osmotic device manufactured with a basic gas generating compound. This device in operation releases drug in both an artificial intestinal fluid according to the spirit of the invention.

The method of this invention provides an unique means for delivering numerous drugs that evidence properties that do not easily lend themselves to delivery in an environment having a pH of neutral or lower. While there has been described and pointed out novel features for delivering hard to deliver drugs at controlled and continuous rates, it is to be understood, those versed in the art will appreciate that various modifications, changes and omissions in the method can be made without departing from the spirit of the invention.

We claim:

1. An osmotic device for delivering a drug to an environment of use, said device comprising:
   (a) a shaped laminated wall comprising a lamina formed of a semi-permeable material and a lamina formed of a microporous material, said wall permeable to the passage of an external fluid present in the environment of use and substantially impermeable to the passage of drug, the wall surrounding and forming;
   (b) a compartment containing the drug indomethacin which exhibits a limited solubility in the fluid, and a pharmaceutically acceptable compound selected from the group consisting of carbonates, bicarbonates and mixtures thereof, which compounds are capable of reactively effervescing with fluid present in the environment of use; and,
   (c) a passageway in the wall connecting the compartment and the exterior of the device for delivering (1) the drug in a therapeutically effective amount to the envirionment, and (2) the compound which reacts with fluid in the environment and effervesces, and thereby aids in delivering the drug to the environment over a prolonged period of time.

2. The osmotic device for delivering the drug according to claim 1 wherein the drug is sodium indomethacin trihydrate.

3. The osmotic device for delivering the drug according to claim 1 wherein the drug is delivered in a therapeutically effective amount of 2 milligrams to 15 milligrams per hour.

4. The osmotic device for delivering the drug according to claim 1 wherein the bicarbonate is potassium bicarbonate.

5. The osmotic device for delivering the drug according to claim 1 wherein the carbonate is potassium carbonate.

6. The osmotic device for delivering the drug according to claim 1 wherein the microporous lamina comprises 45% of cellulose acetate having an acetyl content of 39.8%, 27.5% of hydroxypropyl methylcellulose and 27.5% of polyethylene glycol, and the semipermeable lamina comprises 50% of cellulose acetate having an acetyl content of 39.8%, and 50% of cellulose acetate having an acetyl content of 32%.

7. The osmotic device for delivering the drug according to claim 1 wherein the microporous lamina comprises 45% of cellulose acetate having an acetyl content of 39.8%, 45% of sorbitol, and 10% of polyethylene glycol, and the semipermeable lamina comprises 50% of cellulose acetate having an acetyl content of 39.8%, and 50% of cellulose acetate having an acetyl content of 32%.

8. The osmotic device for delivering the drug according to claim 1, wherein (1) the indomethacin exhibits a limited solubility in the fluid and precipitates therein, and wherein (2) the compound reacts with the fluid in the environment and effervesces, which effervescence substantially prevents precipitation of the drug at the passageway of the device over a prolonged period of time.

9. The osmotic device for delivering the drug according to claim 1 wherein the environment of use is a human, and the device is orally admitted into the gastrointestinal tract.

10. The osmotic device for delivering the drug according to claim 1 wherein, when the device is in operation in the environment of use, fluid therefrom is imbibed through the wall into the compartment in a tendency towards osmotic equilibrium, at a rate determined by the permeability of the wall and the osmotic pressure gradient across the wall to form a solution of compound containing the drug, which solution is delivered through the passageway to the environment of use, with the compound effervescing in the environment, and the drug being delivered to the environment in a therapeutically effective amount over a prolonged period of time.

11. An osmotic device for orally delivering a drug to a human, which device comprises:
 (a) a shaped laminated wall comprising a semipermeable lamina and a microporous lamina, said wall permeable to the passage of an external fluid and substantially impermeable to the passage of drug, the wall surrounding and forming:
 (b) a compartment containing from 0.5 milligrams to 3 grams of the drug indomethacin, and from 0.5 milligrams to 3 grams of a pharmaceutically acceptable compound selected from the group consisting of carbonates, bicarbonates and mixtures thereof that are capable of effervescing in the presence of the fluid; and,
 (c) a passageway in the wall for delivering from the device at a controlled and continuous rate, a therapeutically effective amount of the drug, and an amount of the compound for reactively effervescing with the fluid over a prolonged period of time.

12. The osmotic device for orally delivering the drug according to claim 11 wherein the device is orally admitted into the gastrointestional tract and the fluid is gastric fluid.

13. The osmotic device for orally delivering the drug according to claim 11 wherein the carbonate is a member selected from the group consisting of lithium carbonate, sodium carbonate, potassium carbonate, ammonium carbonate, magnesium carbonate, calcium carbonate, and mixtures thereof.

14. The osmotic device for orally delivering the drug according to claim 11 wherein the bicarbonate is a member selected from the group consisting of lithium bicarbonate, sodium bicarbonate, potassium bicarbonate, magnesium bicarbonate, calcium bicarbonate, and mixtures thereof.

15. The osmotic device for orally delivering the drug according to claim 11 wherein the indomethacin is sodium indomethacin trihydrate and the compartment contains from 40 milligrams to 250 milligrams of said indomethacin, and the bicarbonate is potassium bicarbonate and the compartment contains from 50 milligrams to 300 millgrams of said bicarbonate.

16. The osmotic device for orally delivering the drug according to claim 11 wherein the indomethacin is sodium indomethacin trihydrate and the compartment contains from 85 milligrams to 125 milligrams thereof, and the bicarbonate is potassium bicarbonate and the compartment contains from 130 milligrams to 190 milligrams thereof.

17. The osmotic device for orally delivering the drug according to claim 11 wherein the indomethacin is sodium indomethacin trihydrate and the compartment contains 105 milligrams thereof, and the bicarbonate is potassium bicarbonate and the compartment contains 142 milligrams thereof.

18. The osmotic device for orally delivering the drug according to claim 11 wherein the indomethacin is sodium indomethacin trihydrate and the compartment contains 105 milligrams thereof, and the bicarbonate is potassium bicarbonate and the comparment contains 158 milligrams thereof.

19. The osmotic device for orally delivering the drug according to claim 11 wherein the microporous lamina comprises cellulose acetate, hydroxypropyl methylcellulose and polyethylene glycol, and the semipermeable lamina comprises cellulose acetate having an acetyl content of 32% and cellulose acetate having an acetyl content of 39.8%.

20. The osmotic device for orally delivering the drug according to claim 11 wherein the microporous lamina comprises cellulose acetate, sorbitol and polyethylene glycol, and the semipermeable lamina comprises cellulose acetate having an acetyl content of 39.8% and cellulose acetate having an acetyl content of 32%.

21. An osmotic device for orally delivering a drug to a human, which device comprises:
 (a) a shaped semipermeable, wall said wall permeable to the passage of an external fluid and substantially impermeable to the passage of drug, the semipermeable wall surrounding and forming:
 (b) a compartment containing from 0.5 milligrams to 3 grams of the drug indomethacin, and from 0.5 milligrams to 3 grams of a pharmaceutically acceptable compound selected from the group consisting of carbonates, bicarbonates and mixtures thereof that are capable of reactively effervescing in the presence of the fluid; and, (c) a passageway in the wall for delivering from the device to the human at a controlled and continuous rate, a therapeutically effective amount of the drug, and an amount of the compound for reactively effervescing with the fluid over a prolonged period of time.

22. The osmotic device for orally delivering the drug according to claim 21 wherein the device is orally admitted into the gastrointestional tract, and the fluid is gastric fluid.

23. The osmotic device for orally delivering the drug according to claim 21 wherein the carbonate is a member selected from the group consisting essentially of lithium carbonate, sodium carbonate, potassium carbonate, ammonium carbonate, magnesium carbonate, calcium carbonate, and mixtures thereof.

24. The osmotic device for orally delivering the drug according to claim 21 wherein the bicarbonate is a member selected from the group consisting of lithium bicarbonate, sodium bicarbonate, potassium bicarbonate, magnesium bicarbonate, calcium bicarbonate, and mixtures thereof.

25. The osmotic device for orally delivering the drug according to claim 21 wherein the indomethacin is sodium indomethacin trihydrate and the compartment contains from 40 milligrams to lb 250 milligrams of said indomethacin, and the bicarbonate is potassium bicarbonate and the compartment contains from 50 milligrams to 300 milligrams of said bicarbonate.

26. The osmotic device for orally delivering the drug according to claim 21 wherein the indomethacin is sodium indomethacin trihydrate and the compartment contains from 85 milligrams to 125 milligrams thereof, and the bicarbonate is potassium bicarbonate and the compartment contains from 130 milligrams to 190 milligrams thereof.

27. The osmotic device for orally delivering the drug according to claim 21 wherein the semipermeable material comprises a selectively permeable polymer selected from the group consisting of cellulose acylate, cellulose diacylate, cellulose triacylate, cellulose acetate, cellulose diacetate, cellulose triacetate, and mixtures thereof.

28. The osmotic device for orally delivering the drug according to claim 21 wherein the semipermeable wall comprises cellulose acetate having an acetyl content of 32% and cellulose acetate having an acetyl content of 39.8%.

29. The osmotic device for orally delivering a drug according to claim 21 wherein semipermeable wall comprises 50% of cellulose acetate having an acetyl content of 32%, and 50% of cellulose acetate having an acetyl content of 39.8%.

* * * * *

UNITED STATES PATENT OFFICE
CERTIFICATE OF CORRECTION

PATENT NO. : 4,265,874
DATED : May 5, 1981
INVENTOR(S) : Bonsen, Pieter; Wong, Patrick Seck-Lai; Theeuwes, Felix It is certified that error appears in the above-identified patent and that said Letters Patent are hereby corrected as shown below:

Column 12, Line 2, Claim 25:

Reads: contains from 40 milligrams to lb 250 milligrams of said

SHOULD READ: contains from 40 milligrams to 250 milligrams of said

Signed and Sealed this

Eleventh Day of August 1981

[SEAL]

Attest:

GERALD J. MOSSINGHOFF

Attesting Officer    Commissioner of Patents and Trademarks